United States Patent [19]

Chen et al.

[11] Patent Number: 5,057,522
[45] Date of Patent: Oct. 15, 1991

[54] ANTI-HYPERSENSITIVE N2-TETRAZOLE-β-GLUCURONIDE ANALOG

[75] Inventors: Shieh-Shung T. Chen, Morganville; George Doss, Westfield, both of N.J.

[73] Assignee: Merck & Co., Inc., Rahway, N.J.

[21] Appl. No.: 564,639

[22] Filed: Jul. 19, 1990

[51] Int. Cl.⁵ .................. A61K 31/435; C07D 471/04
[52] U.S. Cl. .................................. 514/303; 546/118; 435/119
[58] Field of Search ....................... 546/118; 514/303

[56] References Cited

U.S. PATENT DOCUMENTS 4,880,804 11/1989 Carini et al. .................... 514/234.5

Primary Examiner—Bernard I. Dentz
Attorney, Agent, or Firm—Joseph F. DiPrima; William H. Nicholson

[57] ABSTRACT

Fermentation of the microorganism Streptomyces sp. MA6751 in the presence of

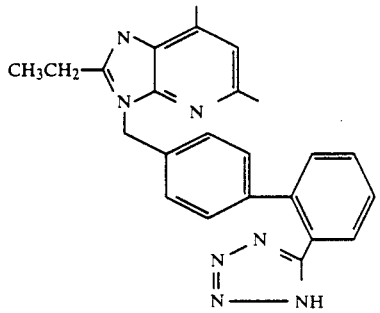

yields an anti-hypertensive compound of the structure 3 Claims, 2 Drawing Sheets

ANTI-HYPERSENSITIVE N2-TETRAZOLE-β-GLUCURONIDE ANALOG

BACKGROUND OF THE INVENTION

1. Field of the Invention

This invention relates to a novel process for the preparation of the antihypertensive agent, compound (I)

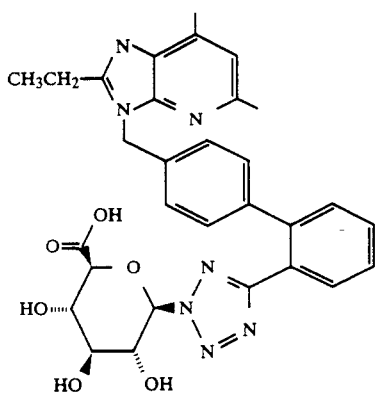

comprising fermentation of compound (II)

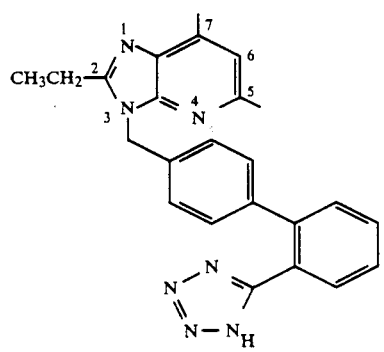

with the microorganism Streptomyces sp. MA6751. Compound (I) and its precursor (II) are Angiotensin II (A II) receptor antagonists useful in the treatment of human hypertensive diseases.

A II is an octapeptide hormone produced mainly in the blood during the cleavage of Angiotensin I by angiotensin converting enzyme (ACE). ACE is localized on the endothelium of blood vessels of lung, kidney and many other organs. A II is the end product of the renin-angiotensin system (RAS), a system that plays a central role in the regulation of normal blood pressure and seems to be critically involved in hypertension development and maintenance, as well as congestive heart failure. A II is a powerful arterial vasoconstrictor that exerts its action by interacting with specific receptors present on cell membranes. A II receptor antagonism is one of the possible modes of controlling the RAS.

2. Brief Description of Disclosures in the Art

Copending U.S. application Ser. No. 516,286, filed May 4, 1990, discloses the substrate compound used in this invention and designated herein as compound (II).

SUMMARY OF THE INVENTION

Figure 1:
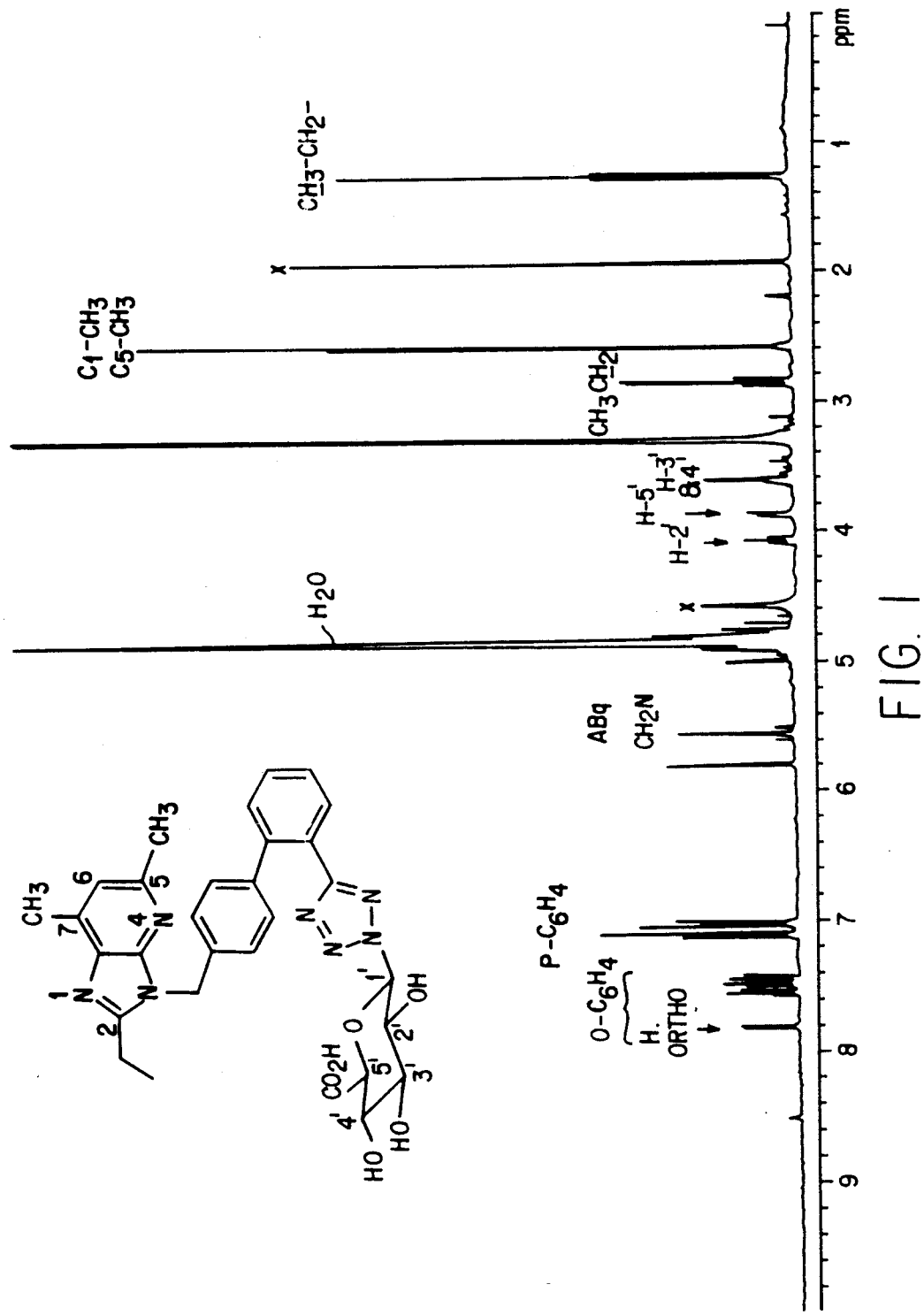
FIG. 1 is an $^1H$ nuclear magnetic resonance (NMR) spectrum taken at 400 MHz of compound (I) in $CD_3OD$.
Figure 2:
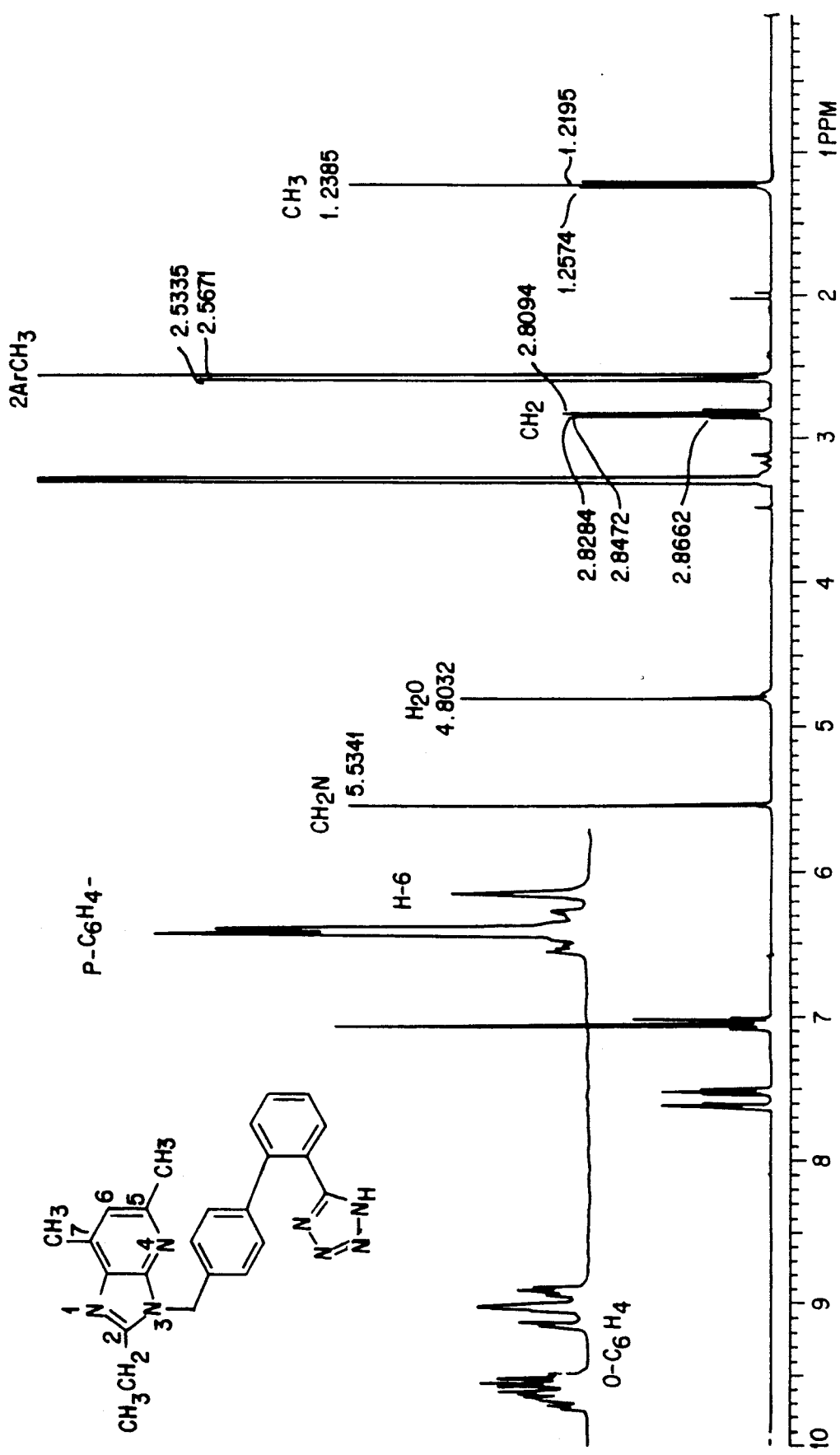
FIG. 2 is an $^1H$ NMR spectrum taken at 400 NMz of compound (II) in $CD_3OD$.

A new antihypertensive biotransformation product (I) is obtained by the fermentation of the microorganism Streptomyces sp. A 6751, in the presence of substrate compound (II). The biotransformation is accomplished under submerged aerobic conditions in an aqueous carbohydrate medium containing a nitrogen nutrient at a pH of about 7 for a sufficient time to produce compound (I).

The resultant N2-tetrazole β-glucuronide analog exhibits A II antagonist activity, i.e., it has an inhibitory concentration ($IC_{50}$) of less than 50 μm in an assay that measures the concentration of potential A II antagonist needed to achieve 50% displacement of the total $^{125}I$-$Sar^1Ile^8$-angiotensin II specifically bound to a membrane preparation derived from rabbit aortae, and therefore it is an antihypertensive agent. This assay is also referred to herein as the "$IC_{50}$" assay.

Also provided by this invention is a pharmaceutical composition containing a therapeutically effective amount of compound (I) in combination with a pharmaceutically acceptable non-toxic carrier or excipient.

In addition, there is provided a method of treating a human host to control hypertensive disorders or for treating congestive heart failure comprising administering to said host a therapeutically effective amount of compound (I).

DETAILED DESCRIPTION OF THE INVENTION AND PREFERRED EMBODIMENTS

The product of this invention is compound (I):

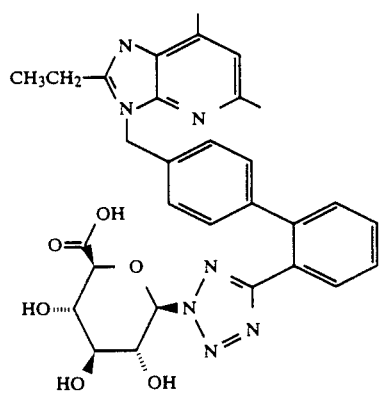

The novel process of this invention comprises fermentation of the microorganism Streptomyces sp. MA6751 in the presence of substrate compound (II)

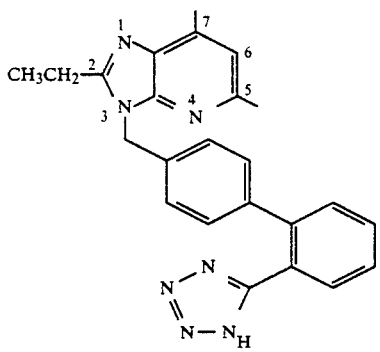

in a nutrient medium, and isolation of the resulting biotransformation product, compound (I), in a conventional manner. A biologically pure sample of Streptomyces sp. MA6751 is currently available in the permanent culture collection of the American Type Culture Collection, 12301 Parklawn Drive in Rockville, Maryland, from which it is available under the Accession Number ATCC 55043.

The following is a general description of Streptomyces sp. strain MA6751. Observations of growth, general cultural characteristics and carbon source utilization were made in accordance with the methods of Shirling and Gottleib (*Internat. J. System. Bacteriol.* 16: 313–340). Chemical composition of the cells was determined using the methods of Lechevalier and Lechevalier (in *Actinomycete Taxonomy.* A. Dietz and D. W. Thayer, Ed. Society of Industrial Microbiology, 1980). Coloration of the culture was determined by comparison with color standards contained in the Inter-Society color Council-National Bureau of Standards Centroid Color Charts (U.S. Dept. of Commerce National Bureau of Standards supplement to NBS Circular 553, 1985).

Source

The culture was isolated from soil at Heather forest, 9000–13,400 ft. elevation. MT. Kilimanjaro, Kenya.

Analysis of Cell Wall Composition

Peptidoglycan contains L-diaminopimelic acid. Whole cell analysis of carbohydrates reveals galactose, glucose, mannose and xylose.

General Growth Characteristics

Good growth on yeast malt extract, (w/o trace elements), glycerol asparagine, inorganic salts-starch, oatmeal, sporulation, and trypticase soy agars. Growth occurs at 27° and 37° C. Culture also grows well in liquid media such as yeast dextrose broth.

Colony Morphology (on Yeast Malt Extract Agar)

Substrate mycelium is orange (71 m.OY) and colonies are opaque, raised, lobate and rubbery. The colony surface is rough textured. Aerial mycelia appear after 4 days incubation and are white in color (263 White). Spore mass, when present, is white (263 White).

Micromorphology

Aerial mycelium (0.57–0.76 μm dia.) arises from a substrate mycelium and is branched and flexous. In mature cultures, the aerial mycelium commonly terminates in spores borne predominantly in spirals and flexous chains.

Miscellaneous Physiological Reactions

Culture does not produce melanoid pigments in tryptone yeast extract broth, and yellow, non-pH dependant diffusible pigment is produced on glycerol asparagine agar. Starch is hydrolzed.

| Cultural Characteristics of Streptomyces sp. MA6751 at 21 Days | | | | |
|---|---|---|---|---|
| Medium | Amount Growth | Aerial Mycelium and/or Spores | Soluble Pigments | Reverse Color |
| Yeast Extract-Malt Extract | good | White (263), spiral sporophores | none noted | Yellow (s.Y 87) |
| Glucose-Asparagine | good | White (263), spiral sporophores | Yellow, non-pH dependent | Yellow (p.Y 89) |
| Inorganic Salts-Starch | good | White (263), spiral sporophores | none noted | Yellow (p.Y 89) |
| Oatmeal | good | White (263), spiral sporophores | none noted | Yellow (m.OY 84) |

| Carbohydrate Utilization Pattern of Streptomyces sp. MA6751 at 21 Days | |
|---|---|
| Carbon Source | Utilization* |
| D-arabinose | 0 |
| L-arabinose | 1 |
| cellobiose | 2 |
| D-fructose | 2 |
| inositol | 2 |
| α-D-lactose | 2 |
| β-D-lactose | 2 |
| D-maltose | 2 |
| D-mannitol | 3 |
| D-raffinose | 2 |
| L-rhamnose | 2 |
| sucrose | 2 |
| D-xylose | 2 |
| L-xylose | 0 |
| α-D-glucose (control) | 3 |

*3 = good utilization
2 = moderate utilization
1 = poor utilization
0 = no utilization In general, compound (I) can be produced by culturing (fermenting) the above-described microorganism in the presence of an appropriate concentration of substrate compound (II) in an aqueous nutrient medium containing sources of assimilable carbon and nitrogen, preferably under submerged aerobic conditions (e.g., shaking culture, submerged culture, etc.). An appropriate concentration of the parent compound in the aqueous medium ranges from 0.05 mg/ml to 0.2 mg/ml, preferably 0.1 mg/ml; less than 0.05 mg/ml is inefficient and greater than 0.2 mg/ml can inhibit the culture. The aqueous medium is incubated at a temperature between 26° C. and 29° C., preferably 27° C.; culture growth will be inhibited below this temperature range and culture death will occur above this temperature range. The aqueous medium is incubated for a period of time necessary to complete the biotransformation as monitored by HPLC, usually for a period of about 24 hours, on a rotary shaker operating at about 220 rpm. with a throw of about 2 in. The aqueous medium is maintained at a pH between 6 and 8, preferably about 7, at the initiation and termination (harvest) of the fermentation process.

A higher or lower pH will cause the culture to die. The desired pH may be maintained by the use of a buffer such as morpholinoethanesulfonic acid (MES), morpholino-propanesulfonic acid (MOPS), and the like, or by choice of nutrient materials which inherently possess buffering properties, such as production media described herein below.

The preferred sources of carbon in the nutrient medium are certain carbohydrates such as glucose, xylose, galactose, glycerin, starch, dextrin, and the like. Other sources which may be included are maltose, rhamnose, raffinose, arabinose, mannose, salicin, sodium succinate, and the like.

The preferred sources of nitrogen are yeast extract, meat extract, peptone, gluten meal, cottonseed meal, soybean meal and other vegetable meals (partially or totally defatted), casein hydrolysates, soybean hydrolysates and yeast hydrolysates, corn steep liquor, dried yeast, wheat germ, feather meal, peanut powder, distiller's solubles, etc., as well as inorganic and organic nitrogen compounds such as ammonium salts (e.g. ammonium nitrate, ammonium sulfate, ammonium phosphate, etc.), urea, amino acids, and the like.

The carbon and nitrogen sources, though advantageously employed in combination, need not be used in their pure form because less pure materials which contain traces of growth factors and considerable quantities of mineral nutrients are also suitable for use. When desired, there may be added to the medium mineral salts such as sodium or calcium carbonate, sodium or potassium phosphate, sodium or potassium chloride, sodium or potassium iodide, magnesium salts, copper salts, cobalt salts, and the like. If necessary, especially when the culture medium foams seriously, a defoaming agent, such as liquid paraffin, fatty oil, plant oil, mineral oil or silicone may be added.

Submerged aerobic cultural conditions are preferred for the production of compound (I) in massive amounts. For the production in small amounts, a shaking or surface culture in a flask or bottle is employed. Furthermore, when the growth is carried out in large tanks, it is preferable to use the vegetative form of the organism for inoculation in the production tanks in order to avoid growth lag in the process of production of compound (I). Accordingly, it is desirable first to produce a vegetative inoculum of the organism by inoculating a relatively small quantity of culture medium with spores or mycelia of the organism product in a "slant" and culturing said inoculated medium, also called the "seed medium", and then to transfer the cultured vegetative inoculum aseptically to large tanks. The fermentation medium, in which the inoculum is produced, is substantially the same as or different from the medium utilized for the production of compound (I) and is generally autoclaved to sterilize the medium prior to inoculation. The fermentation medium is generally adjusted to a pH between 6 and 8, preferably about 7, prior to the autoclaving step by suitable addition of an acid or base, preferably in the form of a buffering solution. Temperature of the seed medium is maintained between 26° C. and 29° C., preferably 27° C.; culture growth will be inhibited below this range and culture death will occur above this range. Incubation of the seed medium is usually conducted for a period of about 10 to 30 hours, preferably 24 hours, on a rotary shaker operating at 220 rpm; the length of incubation time may be varied according to fermentation conditions and scales. Agitation and aeration of the culture mixture maybe accomplished in a variety of ways. Agitation may be provided by a propeller or similar mechanical agitation equipment, by revolving or shaking the fermentor, by various pumping equipment or by the passage of sterile air through the medium. Aeration may be effected by passing sterile air through the fermentation mixture.

Preferred culturing/production media for carrying out the fermentation include the following media:

|  | g/l |
|---|---|
| Seed Medium A | |
| Dextrose | 1.0 |
| Dextrin | 10.0 |
| Beef Extract | 3.0 |
| Ardamine pH | 5.0 |
| NZ Amine Type E | 5.0 |
| $MgSO_4 \cdot 7H_2O$ | 0.05 |
| $K_2HPO_4$ | 0.3 |
| Adjust pH to 7.1 | |
| Add $CaCO_3$ 0.5 g/l | |
| Transformation Medium B | |
| Glucose | 10 |
| Hycase SF | 2 |
| Beef Extract | 1 |
| Corn Steep Liquor | 3 |
| Adjust pH to 7.0 | |

The product, compound (I), can be recovered from the culture medium by conventional means which are commonly used for the recovery of other known biologically active substances. Compound (I) is found in the cultured mycelium and filtrate, which are obtained by filtering or centrifuging the cultured broth, and accordingly can be isolated and purified from the mycelium and the filtrate by a conventional method such as concentration under reduced pressure, lyophilization, extraction with a conventional solvent, such as methylene chloride and the like, pH adjustment, treatment with a conventional resin (e.g. anion or cation exchange resin, non-ionic adsorption resin, etc.), treatment with a conventional adsorbent (e.g. activated charcoal, silicic acid, silica gel, cellulose, alumina, etc.), crystallization, recrystallization, and the like. A preferred recovery method is solvent extraction, particularly using methylene chloride. A preferred purification method involves the use of chromatography, especially high performance liquid chromatography (HPLC), using a silica gel column and an eluant mixture composed of water and an organic solvent such as methanol, acetonitrile and the like, and a small amount of acid such as acetic acid, trifluoroacetic acid, phosphoric acid and the like. A preferred eluant is composed of acetonitrile and water containing 0.1% trifluoroacetic acid, and is run through the column in a linear gradient.

The compound of this invention forms salts with various inorganic and organic acids and bases which are also within the scope of the invention. Such salts include ammonium salts, alkali metal salts like sodium and potassium salts, alkaline earth metal salts like the calcium and magnesium salts, salts with organic bases, e.g., dicyclohexylamine salts, N-methyl-D-glucamine, salts with amino acids like arginine, lysine and the like. Also, salts with organic and inorganic acids may be prepared, e.g., HCl, HBr, $H_2SO_4$, $H_3PO_4$, methane-sulfonic toluene-sulfonic, maleic, fumaric, camphorsulphonic. The non-toxic, physiologically acceptable salts are preferred.

The salts can be formed by conventional means such as by reacting the free acid or free base forms of the product with one or more equivalents of the appropriate acid or base in a solvent or medium in which the salt is insoluble, or in a solvent such as water which is then removed under vacuum or by freeze-drying, or by exchanging the cations of an existing salt for another cation on a suitable ion exchange resin.

Suitable formulations of the material may also include conventional pharmaceutically acceptable biolabile ester of compounds (I) formed via the hydroxy groups or carboxy group on the molecule, such as the acetate.

The product of this invention, compound (I), exhibits A II antagonist activity by the $IC_{50}$ assay, and therefore is useful in treating hypertension. It is also of value in the management of acute and chronic congestive heart failure. This compound may also be expected to be useful in the treatment of secondary hyperaldosteronism, primary and secondary pulmonary hyperaldosteronism, primary and secondary pulmonary hypertension, renal failure such as diabetic nephropathy, glomerulonephritis. scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The product of this invention is also useful for cognitive function enhancement. The application of the compound of this invention for these and similar disorders will be apparent to those skilled in the art.

The compound of this invention is also useful to treat elevated intraocular pressure and to enhance retinal blood flow and can be administered to patients in need of such treatment with typical pharmaceutical formulations such as tablets, capsules, injectables, as well as topical ocular formulations in the form of solutions, ointments, inserts, gels, and the like. Pharmaceutical formulations prepared to treat intraocular pressure would typically contain about 0.1 to 15% by weight, preferably 0.5% to 2% by weight, of the compound of this invention.

In the management of hypertension and the clinical conditions noted above, the compound of this invention may be utilized in compositions such as tablets, capsules or elixirs for oral administration, suppositories for rectal administration, sterile solutions or suspension for parenteral or intramuscular administration, and the like. The compounds of this invention can be administered to patients (animals and human) in need of such treatment in dosages that will provide optimal pharmaceutical efficacy, Although the dose will vary from patient to patient depending upon the nature and severity of disease, the patient's weight, special diets then being followed by a patient, concurrent medication, and other factors which those skilled in the art will recognize, the dosage range will generally be about 1 to 1000 mg. per patient per day which can be administered in single or multiple doses. Perferably, the dosage range will be about 2.5 to 250 mg. per patient per day; more preferably about 2.5 to 75 mg. per patient per day.

The compound of this invention can also be administered in combination with other antihypertensives such as α-methyldopa, and/or diuretics such as hydrochlorothiazide, and/or antiotensin converting enzyme inhibitors such as enalapril, and/or calcium channel blockers such as nifedipine. Typically, the individual daily dosages for these combinations can range from about one-fifth of the minimally recommended clinical dosages to the maximum recommended levels for the entities when they are given singly. These dose ranges can be adjusted on a unit basis as necessary to permit divided daily dosage and, and as noted above, the dose will vary depending on the nature and severity of the disease, weight of the patient, special diets and other factors. Typically, these combinations can be formulated into pharmaceutical compositions as discussed below.

About 1 to 100 mg. of compound (I) of a physiologically acceptable salt thereof is compounded with a physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

Illustrative of the adjuvants which can be incorporated in tablets, capsules and the like are the following: a binder such as gum tragacanth, acacia, corn starch or gelatin; an excipient such as microcrystalline cellulose, a disintegrating agent such as corn starch, a pregelatinzed starch, alginic acid and the like; a lubricant such as magnesium stearate; a sweetening agent such as sucrose, lactose or saccharin; a flavoring agent such as peppermint, oil of wintergreen or cherry. When the dosage unitform is a capsule, it may contain, in addition to materials of the above type, a liquid carrier such as fatty oil. Various other materials may be present as coatings or to otherwise modify the physical form of the dosage unit. For instance, tablets may be coated with shellac, sugar or both. A syrup or elixir may contain the active compound, sucrose as a sweetening agent, methyl and propyl parabens as preservatives, a dye and a flavoring such as cherry or orange flavor.

Sterile compositions for injection can be formulated according to conventional pharmaceutical practice by dissolving or suspending the active substance in a vehicle such as water for injection, a naturally occuring vegetable oil like sesame oil, coconut oil, peanut oil, cottonseed oil, etc., or a synthetic fatty vehicle like ethyl oleate or the like. Buffers, preservatives, antioxidants and the like can be incorporated as required.

RECEPTOR BINDING ASSAY USING RABBIT AORTAE MEMBRANE PREPARATION

Three frozen rabbit aortae (obtained from Pel-Freeze Biologicals) were suspended in 5 mM Tris-0.25M Sucrose, pH 7.4 buffer (50 ml) homogenized, and then centrifuged. The mixture was filtered through a cheesecloth and the supernatant was centrifuged for 30 minutes at 20,000 rpm at 4° C. The pellet thus obtained was resuspended in 30 ml of 50 mM Tris-5 mM $MgCl_2$ buffer containing 0.2% Bovine Serum Albumin and 0.2 mg/ml Bacitration and the suspension was used for 100 assay tubes. Samples tested for screening were done in duplicates. To the membrane preparation (0.25 ml) there was added $^{125}$I-Sar$^1$Ile$^8$-angiotensin II [obtained from New England Nuclear] (10 ul; 20,000 cpm) with or without the test sample and the mixture was incubated at 37° C. for 90 minutes. The mixture was then diluted with ice-cold 50 mM Tris-0.9% NaCl, pH 7.4 (4 ml) and filtered through a glass fiber filter (GF/B Whatman 2.4" diameter). The filter was soaked in scintillation cocktail (10 ml) and counted for radioactivity using Packard 2660 Tricarb liquid scintillation counter. The inhibitory concentration ($IC_{50}$) of potential AII antagonist which gives 50% displacement of the total specifically bound 125I-Sar1Ile8-angiotension II was presented as a measure of the efficacy of such compounds as AII antagonists.

Using the methodology described above, the compound of this invention was evaluated and was found to exhibit an activity of at least $IC_{50} < 50$ μm thereby demonstrating and confirming the utility of the compound of this invention as an effective AII antagonist.

Preparation of Substrate Compound (II):
5,7-Dimethyl-2-ethyl-3-(2'-(tetrazol-5-yl)biphen-4-yl)methyl-3H-imidazol]4,5-b[pyridine I. Preparation of
N-Triphenylmethyl-5-(4'-bromomethyl-biphen-2-yl)tetrazole Step 1: 2-cyano-4'-methylbiphenyl To a solution of p-bromotoluene (30 g) in dry ether (150 ml) at −78° C., a solution of t-BuLi in pentane (1.7 M) (210 ml) was added slowly over a period of 1 hour and 30 minutes, using a dropping funnel. The bath was then removed and the mixture was stirred at room temperature for an additional 2 hours. The content of the flask was then added slowly (using a cannula) at room temperature to a premixed solution of $ZnCl_2$ in ether (1 M) (180 mL) and dry THF (360 mL). The mixture was stirred for 2 hours at that temperature and the slurry was added (using a cannula) to a solution of 2-bromobenzonitrile (21.3 g) and $NiCl_2(Ph_3P)_2$ (2.1 g) in dry THF (300 ml). The mixture, after stirring at room temperature overnight (18 hours), was poured slowly with stirring into ice cold 0.5 N HCl (1500 ml). The organic layer was separated, and the aqueous phase was extracted with ether (3×300 ml). The combined organic layer was washed with water, brine and then dried over $MgSO_4$. Removal of the solvent gave the crude product as a semisolid mass (34 g). The material was purified on a silica gel flash column using ethylacetate/hexane (1:12) to give the desired nitrile as a low melting solid (28 g, 88%). NMR ($CDCl_3$) δ2.42 (s, 3H), 7.2-7.8 (m, 8H); FAB-MS: m/e 194 (M+H).

Step 2: Trimethylstannyl azide

To a concentrated solution of $NaN_3$ (40 g) in water (100 ml), a solution of trimethylthin chloride (20 g) in dioxane (10 ml) was added in three portions under vigorous stirring. An instantaneous precipitate formation was observed. The mixture, after stirring overnight at room temperature, was filtered. The residue was washed with water, and dried under suction and then in vacuo over $P_2O_5$. Yield 18.7 g (81%), mp 132°-136° C.

Step 3:
N-triphenylmethyl-5-(4'-bromomethyl-biphen-2-yl)tetrazole

The titled compound was prepared starting from 2-cyano-4'-methylbiphenyl (Step 1) as described in European patent Application EP 0,291,969.

II. Preparation of
5,7-Dimethyl-2-ethylimidazo[4,5-b]pyridine

Step 1: 2-Amino-4,6-dimethyl-3-nitropyridine

2-Amino-4,6-dimethylpyridine (10.0 g, 81.8 mmol) was added portion-wise to 65 mL of $H_2SO_4$ (conc. d=1.84) which was stirred (mechanical) at 0° C. After complete addition, the mixture was warmed to room temperature until the mixture become homogeneous. The solution was then cooled to −10° C. and a precooled (0° C.) mixture of concentrated $HNO_3$ (11.5 mL, d=1.40) and $H_2SO_4$ (8.2 mL, d=1.84) was added at such a rate as not to raise the internal reaction temperature above −9° C. Ten minutes after the addition was complete this cooled (−10° C.) mixture was poured onto 400 g of crushed ice. The resulting slurry was neutralized by the addition of conc $NH_4OH$ (to pH 5.5) while cooling (ice bath). The solid was isolated by filtration, and dried at room temperature to give 13.3 g of 2-nitramino-4,6-dimethylpyridine as a white solid.

To 75 mL of stirred conc $H_2SO_4$ cooled to −5° C. (ice-salt bath) was added 4,6-dimethyl-2-nitraminopyridine (13.2 g, 79 mmol) portion-wise at such a rate as to maintain the internal temperature below −3° C. The mixture was warmed to 0° C. until homogeneous (30 minutes) at which time tlc ($SiO_2$, 1:1 EtOAc/hexanes on a $NH_4OH$ neutralized aliquot) indicated that the rearrangement was complete. The mixture was poured onto 400 g of crushed ice and the pH was adjusted to 5.5 by the addition of concentrated $NH_4OH$. The resulting yellow slurry was cooled to 0° C., filtered, washed with cold water (50 mL), and dried at room temperature to give 10.32 g of a mixture of the title compound and the 5-nitro isomer in a 55:45 ratio (determined by $^1H$ NMR). This mixture was used directly in Step 2.

Step 2: 5,7-Dimethyl-2-ethylimidazo[4,5-b]pyridine

To a mixture of 8.44 g of a 55:45 mixture of 2-Amino-3-nitro-4,6-dimethylpyridine and 2-Amino-4,6-dimethyl-5-nitropyridine in MeOH (1.2 L) was added 10% Pd/C (2.4 g). The reaction vessel was evacuated then purged with $H_2$ at 1 atm. and stirred vigorously for 18 hours. Filtration (celite), and concentration gave 6.65 g of a mixture of 2,3-diamino-4,6-dimethylpyridine and 2,5-diamino-4,6-dimethylpyridine as a dark solid. To 5.40 g (39.4 mmol) of this mixture was added propionic acid (8.80 mL, 118 mmol) followed by polyphosphoric acid (100 mL). This stirred mixture was heated to 90° C. for 3 hours then to 100° C. for 1 hour. After the reaction was complete, the warm mixture was poured onto 300 g of ice and the mixture was made basic with $NH_4OH$. The mixture was extracted (4×50 mL $CH_2Cl_2$), dried ($K_2CO_3$) and concentrated to give a mixture of the title compound and 4,6-dimethyl-2,5-bis(propionamido)pyridine. Purification ($SiO_2$, 5% MeOH/ EtOAc) gave 1.66 g of the tilte compound as the slower eluting component. $^1H$ NMR ($CD_3OD$, 300MHz) δ6.95 (s, 1H), 2.92 (q, 2H, J=7.8 Hz), 2.54 (apparent s, 6H), 1.40 (t, 3H, J=7.8 Hz)

III.
5,7-Dimethyl-2-ethyl-3-(2'-(tetrazol-5-yl)biphen-4-yl)methyl-3H-imidazo[4,5-b]-pyridine Part A To a stirred suspension of NaH (17.2 mmol of an 80% dispersion) in dry dimethylformamide (30 mL) at rt was added 5.7-dimethyl-2-ethylimidazo[4,5-b]pyridine (1.51 g, 8.62 mmol) in one portion. After 20 minutes, the mixture was cooled to 0° C. and N-triphenylmethyl-5-(4'-bromomethylbiphenyl-2-yl)-tetrazole (5.29 g, 9.48 mmol) was added in one portion. The resulting mixture was warmed to rt and stirred for 15 hours. The excess NaH was quenched with water and the bulk of the DMF was removed in vacuo at 40°-50° C. The residue was extracted with EtOAc from brine, dried ($K_2CO_3$), and concentrated. Purification by flash chromatography ($SiO_2$, solvent gradient: 80% EtOAc/hexanes, 100% EtOAc) gave 4.25 g of 5,7-dimethyl-2-ethyl-3-(2'-

(N-triphenylmethyltetrazol-5-yl)biphen-4-yl)methyl-3H-imidazo[4,5-b]pyridine: $^1$H NMR (300 MHz, CDCl$_3$) δ7.86 (dd, 1H, J=7, 2 Hz), 750–7.41 (m, 2H), 7.36–721 (m, 10 H), 7.05 (d, 2 H, J=4.5 Hz), 6.95–6.89 (m, 7 H), 6.86 (d, 2 H, J=4.5 Hz), 5.35 (s, 2H), 2.67 (q, 2 H, J=7.5 Hz), 2.65 (s, 3 H), 2.58 (s, 3 H), 1.25 (t, 3 H, J=7.5 Hz).

Part B

To a stirred solution of the tritylprotected tetrazole (4.13 g, 6.33 mmol) in CH$_2$Cl$_2$ (40 mL) at room temperature was added 85% formic acid (60 mL). After 45 minutes, the mixture was concentrated and the residue was purified by chromatography (SiO$_2$, 85:13.5:1.5 CHCl$_3$-MeOH-NR$_4$OH) followed by crystallization from 30 mL of MeOH to give 2.18 g (84%) solid: mp 156°–158° C. $^1$H NMR (300 MHz, CD$_3$OH) δ7.68–7.61 (m, 2 H), 7.57–7.50 (m, 2 H), 7.07 (apparent singlet, 4 H), 7.04 (s, 1H), 5.55 (s, 2 H), 2.85 (Q, 2 H, J=7.5 Hz), 2.61 (s, 3 H), 2.58 (s, 3 H), 1.25 (t, 3 H, J=7.5 Hz).

Anal. Calcd for C$_{24}$H$_{23}$N$_7$.0.25 H$_2$O: C, 69.63; H, 5.72; N, 23,68. Found: C, 69.91; H, 5.73; N, 23.60.

The following examples are given for the purpose of illustrating the present invention and should not be construed as being limitations on the scope or spirit of the instant invention.

EXAMPLE 1

Microorganism and Culture Conditions

A frozen vial (2.0 ml) of culture MA 6751 (ATCC No. 55043) was used to inoculate a 250 ml baffled shake flask containing 50 ml of an autoclaved (sterilized) seed medium consisting of (in units of grams/liter) dextrin 10.0, dextrose 1.0, beef extract 3.0, ardamine PH (Yeast Products, Inc.) 5.0, N-Z Amine type E 5.0, MgSO$_4$.7-H$_2$O 0.05, K$_2$HPO$_4$ 0.3, and CaCO$_3$ 0.5. The pH of the seed medium was adjusted to 7.1 before autoclaving. The seed was incubated in the seed medium at 27° C. for 24 hours on a rotary shaker operating at 220 rpm. A 2.5 ml aliquot of the resulting seed medium was used to inoculate each of two 250 ml non-baffled shake flasks, each flask containing 50 ml of the following previously autoclaved (sterilized) transformation medium B.* Substrate compound (II) was added to each flask as an aqueous solution with pH of 8 to achieve a final concentration of 0.1 mg/ml. The shake flask contents were subsequently incubated for 24 hours at 27° C. on a rotary shaker operating at 220 rpm. The resultant broths were combined for isolation and purification.

*1. Transformation medium B consisted of (in grams/liter) glucose 10.0; Hycase SF 2.0; beef extract 1.0; corn steep liquor 3.0; l where the pH was adjusted to 7.0 before autoclaving.

Isolation and Purification Procedure for the Broth

The whole broth (105 ml) of transformation media B was acidified to pH 2.0 and then extracted three times with methylene chloride (3×100 ml). Methylene chloride extracts were combined, dried over sodium sulfate, and concentrated under vacuum to an oily residue. The residue was dissolved in methanol and subjected to high performance liquid chromatography (HPLC) purification.

HPLC was carried out on Whatman Partisil 10 ODS-3, 9.4 mm×25 cm column at room temperature and monitored at 255 nm and 275 nm. The column was developed at 3 ml/min with linear gradient from 0.1% aqueous TFA-CH$_3$CN, 85:15 to 0.1% aqueous TFA-CH$_3$CN, 15:85 in 60 minutes. The compound was collected during repeated injections of the above described extract. The compound was visible at 255 nm and 275 nm. The fractions at retention time 24.5 minutes were pooled and evaporated to remove solvents to yield 4.0 mg. of compound (I).

Characterization

Compound (I) of this invention was characterized via NMR spectrometry yielding the proton NMR spectrum of FIG. 1, which also contains the assigned molecular structure.

What is claimed:

1. A compound of structural formula (I):

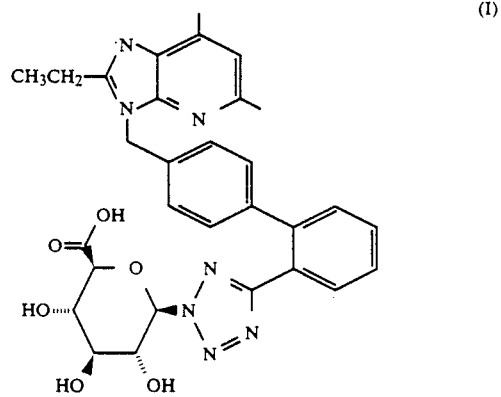

(I)

2. An antihypertensive pharmaceutical composition comprising a non-toxic therapeutically effective amount of the compound of claim 1 and a pharmaceutically acceptable carrier.

3. A method of treating hypertension of congestive heart failure comprising the administration of a non-toxic therapeutically effective amount of the compound of claim 1 to a subject in need of such treatment.

* * * * *